United States Patent
Fayolle et al.

(10) Patent No.: US 10,690,945 B2
(45) Date of Patent: Jun. 23, 2020

(54) METHOD FOR OPTIMIZING AN OPTICAL LENS EQUIPMENT FOR A WEARER

(71) Applicant: Essilor International, Charenton-le-Pont (FR)

(72) Inventors: Romain Fayolle, Charenton-le-Pont (FR); Pascal Allione, Charenton-le-Pont (FR); Sylvain Chene, Charenton-le-Pont (FR); Delphine Tranvouez, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/119,649

(22) PCT Filed: Feb. 17, 2015

(86) PCT No.: PCT/EP2015/053325
§ 371 (c)(1),
(2) Date: Aug. 17, 2016

(87) PCT Pub. No.: WO2015/124574
PCT Pub. Date: Aug. 27, 2015

(65) Prior Publication Data
US 2017/0059886 A1    Mar. 2, 2017

(30) Foreign Application Priority Data
Feb. 18, 2014   (EP) .................................. 14305219

(51) Int. Cl.
*A61B 3/10*   (2006.01)
*A61B 3/14*   (2006.01)
(Continued)

(52) U.S. Cl.
CPC .......... *G02C 13/005* (2013.01); *A61B 3/0041* (2013.01); *A61B 3/112* (2013.01);
(Continued)

(58) Field of Classification Search
CPC ......... G02C 13/005; A61B 3/103; A61B 3/14; A61B 3/113; A61B 3/152; A61B 3/1225;
(Continued)

(56) References Cited

U.S. PATENT DOCUMENTS 5,182,585 A * 1/1993 Stoner ...................... G02B 3/14
351/158
2003/0058406 A1   3/2003 Blum et al.
(Continued)

FOREIGN PATENT DOCUMENTS

| EP | 2693260 A1 | 2/2014 |
|---|---|---|
| WO | 2010130932 A1 | 11/2010 |
| WO | 2014001490 A1 | 1/2014 |

OTHER PUBLICATIONS

International Search Report dated Mar. 18, 2015; International PCT Application No. PCT/EP2015/053325.

*Primary Examiner* — Dawayne Pinkney
(74) *Attorney, Agent, or Firm* — Oblon, McClelland, Maier & Neustadt, L.L.P.

(57) ABSTRACT

Method for optimizing an optical lens equipment for a wearer Method for optimizing an optical lens equipment for a wearer, the method comprising:—an eye tracking device providing step, during which a spectacle frame mounted eye tracking device is provided to the wearer, —a wearer parameter monitoring step, during which at least one parameter relating to the eyes of the wearer is monitored using the eye tracking device and—an optimization step during which the optical lens equipment is optimized based at least partly on the base of the monitoring of the at least one parameter during the wearer parameter monitoring step.

20 Claims, 1 Drawing Sheet

(51) Int. Cl.

| | | |
|---|---|---|
| *A61B 3/02* | (2006.01) | |
| *A61B 3/00* | (2006.01) | |
| *G02C 13/00* | (2006.01) | |
| *G02C 7/02* | (2006.01) | |
| *G02C 7/08* | (2006.01) | |
| *G02C 7/06* | (2006.01) | |
| *G02B 27/01* | (2006.01) | |
| *A61B 3/11* | (2006.01) | |
| *A61B 3/113* | (2006.01) | |

(52) U.S. Cl.
 CPC .......... *A61B 3/113* (2013.01); *G02B 27/0172* (2013.01); *G02C 7/025* (2013.01); *G02C 7/027* (2013.01); *G02C 7/028* (2013.01); *G02C 7/063* (2013.01); *G02C 7/081* (2013.01); *G02C 7/083* (2013.01); *G02B 2027/014* (2013.01)

(58) Field of Classification Search
 CPC ........... A61B 3/024; A61B 3/032; A61B 3/04; A61B 3/1015
 USPC ........ 351/204, 200, 205–206, 209–210, 208, 351/221–223, 233, 246
 See application file for complete search history.

(56) References Cited

U.S. PATENT DOCUMENTS

| | | | |
|---|---|---|---|
| 2005/0036109 A1 | 2/2005 | Blum et al. | |
| 2011/0221657 A1* | 9/2011 | Haddick | G02B 27/017 345/8 |
| 2013/0044291 A1* | 2/2013 | Kato | A61B 3/0025 351/209 |
| 2013/0170017 A1* | 7/2013 | Caldeira | G02B 25/001 359/319 |
| 2015/0126845 A1* | 5/2015 | Jin | G02B 27/017 600/383 |

\* cited by examiner

METHOD FOR OPTIMIZING AN OPTICAL LENS EQUIPMENT FOR A WEARER

The invention relates to a method for optimizing an optical lens equipment for a wearer using an eye tracking device mounted on a spectacle frame.

The discussion of the background of the invention herein is included to explain the context of the invention. This is not to be taken as an admission that any of the material referred to was published, known or part of the common general knowledge at the priority date of any of the claims.

Usually a person needing to wear an ophthalmic lens equipment goes to the premise of an optician for order the ophthalmic lens equipment at a lens provider. When ordering the ophthalmic lens equipment the optician provides to the lens provider at least the prescription of the wearer.

Typically the prescription is a set of optical characteristics of optical power, of astigmatism and, where relevant, of addition, determined by an eye car professional in order to correct the vision defects of an individual, for example by means of a lens positioned in front of his eye.

Some lens providers propose to consider in addition to the prescription further parameters related to the eyes of the wearer when designing the ophthalmic lens. Typically, the interpupillary distance of the wearer can be considered by the lens provider when determining the design of the optical lens to be provided to the wearer.

The further parameters of the wearer are usually measured or determined by the optician at the shop when the wearer is to order the ophthalmic lenses.

Lens providers have developed lenses that can be customized considering more and more parameters relating to the eyes of the wearer. It has been observed that some of the wearer parameters may change over time and/or may depend on the type of activity the wearer is carrying out. More generally it has been observed that measurements of parameters relating to the eyes of a wearer over short periods of time at the optician shop do not always provide very accurate and/or relevant results. In particular, the ophthalmic lenses designed using such parameters may not be perfectly adapted to the wearer.

Therefore there is a need to improve the method of determination of the wearer parameters beside the wearer's prescription so as to improve even more the quality of the proposed ophthalmic lenses.

One object of the invention is to provide a method for optimizing an optical lens equipment, in particular by determining wearer parameter more accurately than with the prior art methods.

To this end, the invention proposes a method for optimizing an optical lens equipment for a wearer, the method comprising:
- an eye tracking device providing step, during which a spectacle frame mounted eye tracking device is provided to the wearer,
- a wearer parameter monitoring step, during which at least one parameter relating to the eyes of the wearer is monitored using the eye tracking device and
- an optimization step during which the optical lens equipment is optimized based at least partly on the base of the monitoring of the at least one parameter during the wearer parameter monitoring step.

Advantageously, using an eye tracking device mounted on a spectacle frame to determine the wearer parameter increases the accuracy and the relevancy of the determined wearer parameter.

First the use of a spectacle frame mounted eye tracking device allows monitoring the wearer parameter over a longer period of time without disturbing the wearer.

Secondly the use of a spectacle frame mounted eye tracking device allows monitoring the wearer parameter while having the wearer carry out various activity, for example the wearer may be reading a book, looking at his smart phone and also playing golf or driving a car.

Thirdly, the use of a spectacle frame mounted eye tracking device allows the wearer to have a natural behavior, to move freely, without having to get a restrictive posture or position imposed by a special measuring device or method for measuring wearer parameters.

Fourthly, the use of a spectacle frame mounted eye tracking device can allow the ametropic wearer to have a natural behavior for a long period of time with his/her correction included in the spectacle, that leads to better measurements than measurements done using specific instruments for which the prescription lenses may prevent any measurement. This is particularly true for progressive wearer because progressive lenses introduce special refractive correction, and wearer behavior/posture may differ greatly if he/she has not his/her corrective lenses during the measurement.

The prior art method for determining the wearer parameter are limited in time, being carried out at the optician's and therefore in a slightly unusual, stressful environment, needs specific and restrictive instruments/methods having impact on wearer behavior, and the type of activity the wearer may carry out are also limited.

The method according to the invention allows monitoring eye related parameters of a wearer over a long period, from a few minutes to a few hours or even over days, in a natural environment corresponding to the environment the wearer is to use his optical equipment, and with no restriction about the position or posture the wearer may adopt.

The method according to the invention can be carried out at the optician store, and allow the wearer to move more freely in the store and adopt a more natural behavior, or in a natural environment, for example during normal life activity, such as driving activity or sport activity.

According to further embodiments which can be considered alone or in combination:
- the method further comprises a visual environment data providing step during which visual environment data indicative of the visual environment of the wearer are provided, and during the optimization step the optical lens equipment is optimized based at least partly on the visual environment data; and/or
- the method further comprises a wearer activity data providing step during which wearer activity data indicative of the activity of the wearer are provided, and during the optimization step the optical lens equipment is optimized based at least partly on the wearer activity data; and/or
- the visual environment of the wearer and/or the activity of the wearer is monitored in a synchronized manner with the wearer parameter so as to link the wearer parameter with the visual environment of the wearer and/or the activity of the wearer; and/or
- the method further comprises a head movement monitoring step during which the head movement of the wearer is monitored in a synchronized manner with the wearer parameter and the visual environment of the wearer and/or the activity of the wearer so as to link the eye-head coordination of the wearer with the visual environment of the wearer and/or the activity of the wearer; and/or during the optimization step the optical function of the optical lens equipment is optimized; and/or during the optimization step the dioptric function of the optical lens equipment is optimized; and/or during the optimization step the transmission function of the optical lens equipment is optimized; and/or during the optimization step a specific optical lens is selected among a list of optical lens on the base of the monitoring of the at least one parameter; and/or during the optimization step the size and/or the mean curvature and/or the thickness and/or the shape of the optical lens is optimized; and/or during the optimization step the position of the optical lens in the optical lens equipment is optimized; and/or the eye tracking device is adapted to determine the gazing direction of the wearer; and/or the eye tracking device is adapted to determine the viewing distance of the wearer; and/or the eye tracking device comprises at least one light detector adapted to acquire images of at least one eye of the wearer; and/or the eye tracking device comprises at least one pair of electrodes adapted to measure the electrical potential on the skin near the eye of the wearer, and an associated processing device configured to detect blinks, saccades, and/or eye movements; and/or the eyetracking device comprises at least an accelerometer and/or a camera taking picture of the environment and/or a light sensor; and/or the method further comprises a display step during which the information relating to the at least one parameter monitored during the monitoring step is displayed to the wearer; and/or the monitoring step, when carried out at the optician store, is carried out during at least one minute; and/or the monitoring step is carried out during at least 10 minutes; and/or the spectacle frame mounted eye tracking device provided to the wearer has a weight smaller than or equal to 100 g; and/or the monitoring step is carried out while having the wearer practice specific activities in a natural environment;

during the monitoring step the amplitude and/or the variation over time and/or the distribution of the at least one parameter is monitored; and/or the at least one wearer parameter monitored during the monitoring step is selected in the list consisting of:
  eye gazing direction,
  pupil diameter,
  pupil shape,
  pupil appearance,
  phoria measurements,
  blinking frequency,
  gazing disparity between both eyes of the wearer
  the convergence distance of the eyes of the wearer,
  the level of illumination of at least one eye of the wearer,
  the intersection of the visual axe of the wearer with at least one surface of the optical lens,
  general eye appearance, such as Iris, cornea, sclera appearance, eye watering, and
  speed of the eye movement.

The invention further relates to a method of manufacturing an ophthalmic lens for a wearer, the method comprising:

an optical function optimization step during which the optical function of the ophthalmic lens is optimized using a method according to the invention, and a manufacturing step during which the optical lens is manufactured.

The invention also relates to a method of controlling an adjustable lens device comprising an adjustable lens, an optical function controller and an eye tracking device, the adjustable lens having an optical function and extending between at least one eye of the wearer and the real world scene when the device is used by the wearer, and the optical function controller being arranged to control the optical function of the adjustable lens, the method comprising:

an optical function optimization step during which the optical function of the adjustable lens is optimized using a method according to the invention, an optical function adapting step during which the optical function of the adjustable lens is adjusted to correspond to the optimized optical function determined during the optical function optimization step.

According to a further aspect, the invention relates to a computer program product comprising one or more stored sequence of instruction that is accessible to a processor and which, when executed by the processor, causes the processor to carry out the steps of the methods according to the invention.

According to another aspect the invention relates to a program which makes a computer execute the method of the invention.

The invention also relates to a computer readable medium carrying one or more sequences of instructions of the computer program according to the invention.

The invention further relates to a computer-readable storage medium having a program recorded thereon; where the program makes the computer execute the method of the invention.

The invention relates to a device comprising a processor adapted to store one or more sequence of instructions and to carry out at least one of the steps of a method according to the invention.

Non limiting embodiments of the invention will now be described with reference to the accompanying drawing wherein.

Elements in the figures are illustrated for simplicity and clarity and have not necessarily been drawn to scale. For example, the dimensions of some of the elements in the figure may be exaggerated relative to other elements to help improve the understanding of the embodiments of the present invention.

Figure 1:
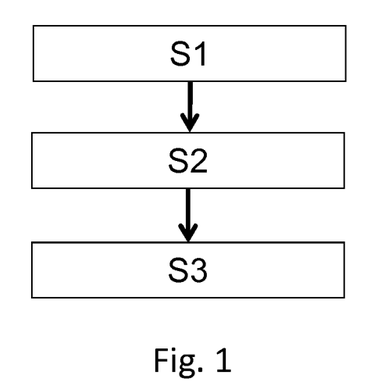
FIG. 1 is a flowchart representing the steps of a method for optimization according to the invention.

As illustrated on FIG. 1, the method for optimizing an optical lens equipment for a wearer according to the invention comprises at least:
  an eye tracking device providing step S1,
  a wearer parameter monitoring step S2, and
  an optimization step S3.

During the eye tracking device providing step S1, an eye tracking device mounted on a spectacle frame is provided to the wearer.

Figure 2:
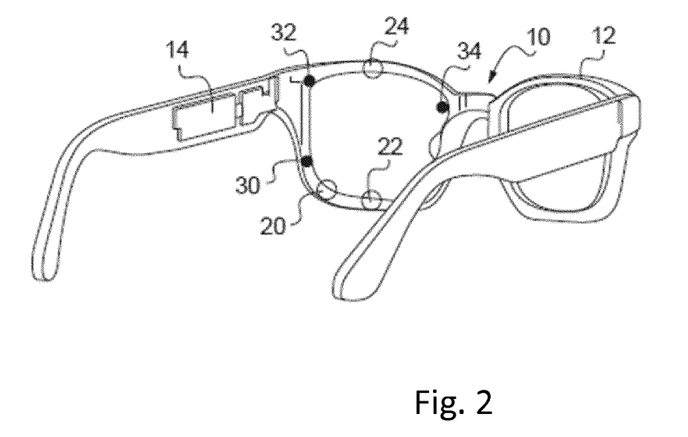
FIG. 2 is a schematic representation of a head mounted eye tracking device that may be used for the optimization method according to the invention.

An example of spectacle frame mounted eye tracking device is represented on FIG. 2.

The eye tracking device 10 represented on FIG. 2 comprises a spectacle frame 12 with three light detector 20, 22, 24 directed at the left eye (not shown) of the wearer.

In the example of FIG. 2 the light detectors 20, 22, 24 are cameras, however, the light detector could also be pixelated light detectors or light detector arrays.

The cameras 20, 22, 24 are arranged to be directed toward the head of the wearer in order to track the locations of the left eye of the wearer, for example the pupils, eyelids, irises, glints, and/or other reference points in the region of the left eye.

The cameras 20, 22, 24 may include charge-coupled device (CCD), complementary metal-oxide-semiconductor (CMOS), or other detectors that include an active area, e.g., including a rectangular or other array of pixels, for capturing images and/or generating video signals representing the images. The active area of each of the cameras 20, 22, 24 may have any desired shape, e.g., a square or rectangular shape, circular, and the like. The surface of the active area of one or more cameras may also be curved, if desired, e.g., to compensate during image acquisition for the nearby three-dimensional curvature of the eye and surrounding structures being imaged.

The eye tracking device 10 may optionally further comprises three illumination sources 30, 32, 34 arranged to as to illuminate the left eye of the wearer when wearing the spectacle frame 12.

The three illumination sources 30, 32, 34 are fixed to the spectacle frame 12. In an exemplary embodiment, illumination sources 30, 32, 34 may include light-emitting diodes (LEDs), organic LEDs (OLEDs), laser diodes, or other devices that convert electrical energy into photons. Each illumination source 30, 32, 34 may be used to illuminate the eye to acquire images using any of the cameras 20, 22, 24 and/or to produce reference glints for measurement purposes to improve gaze-tracking accuracy. In an exemplary embodiment, each light source 30, 32, 34 may be configured for emitting a relatively narrow or wide bandwidth of the light, for example infrared light at one or more wavelengths between about 700-1000 nanometers. For example, AlGaAs LEDs provides an emission peak at 850 nm and are widely used and affordable, while commodity CMOS cameras used in mobile phones and webcams show a good sensibility at this wavelength.

The eye tracking device 10 further comprises a processing unit 14 arranged to receive the images collected by the cameras 20, 22, 24 for further processing or recording in a storage media. The processing unit is arranged in one of the sides of the spectacle frame.

Although not represented, the eye tracking device further comprises a power source, for example a battery and/or other electronics. Advantageously, to distribute weight more evenly within the spectacle frame 12, the power source and/or other electronics may arranged in the side of the spectacle frame opposite to the one containing the processing unit 14.

Advantageously, such head mounted eye tracking device being included in a spectacle frame the wearer may use the eye tracking device over long periods of time without being hindered. For example, such eye tracking device can be used for long period of time measurements so as to determine accurately in everyday life conditions the visual behavior of the wearer.

According to a preferred embodiment of the invention, the eye tracking device provided to the wearer has an overall weight smaller than or equal to 100 g, for example smaller than or equal to 75 g.

Although on FIG. 2 cameras and illumination sources have been represented only on the left side of the spectacle frame, the eye tracking device may very well comprise cameras and illumination sources and/or on the right side of the spectacle frame.

Advantageously, having cameras on both sides of the spectacle frame allows providing accurate information on the gazing direction and distance of the wearer.

Although not represented on FIG. 2, the eye tracking device may comprise in addition to or alternatively to the cameras, at least a pair of electrodes adapted to measure the electrical potential on the skin near the eye of the wearer.

The eye tracking device may further be associated with processing devices configures to detect blinks, saccades and/or eye movements.

The eye tracking device may be obtained by adding eye tracking elements, such as cameras, battery, processing means etc . . . to a standard spectacle frame comprising ophthalmic lenses adapted at least to the prescription of the wearer. This can be in the form an electronic add-on that is attached to the frame.

Alternatively the eye tracking device may comprise a spectacle frame in which ophthalmic lenses adapted at least to the prescription of the wearer are mounted. For example, the eye tracking device may be in the form of an add on device that is attached to the current frame of the wearer equipped with his/her current corrective lenses. In this case, the eye tracking device preferably has cameras integrated between the eye of the wearer and the lens, so as to avoid the refractive deviation coming from the optical power of the lenses, that will cause the image of the eye to be distorted. This allow to have an eyetracking device measurement that will not depend on the ophthalmic lenses Advantageously, the wearer may use the eye tracking device in everyday life situation and the eye related parameters are monitored more accurately.

During the wearer parameter monitoring step S2, at least one parameter relating to the eyes of the wearer is monitored using the eye tracking device provided during the eye tracking device providing step S1.

The longer the monitoring step S2 is carried out the more accurate the monitoring. Typically, the monitoring step is carried out over a period of time of at least 10 minutes. For example, the eye tracking device may be provided to the wearer is the morning and the monitoring step can be carried out all along the day so as to monitor the parameter of the eyes of the wearer over many different visual situations.

If the wearer is monitored at an optician store, the monitoring time can be shortened, but is preferably longer than one minute.

During the monitoring step the amplitude and/or the variation over time and/or the distribution of the at least one parameter relating to the eye of the wearer is monitored. For example, the amplitude of the parameter is determined at a given frequency and stored, for example in an internal memory. The measured and stored data can be used to determine variation over time and/or distribution of the monitored parameter.

So as to increase the pertinence of the monitoring, the monitoring step is carried out while having the wearer practice specific activities in a natural environment corresponding to the usual environment of the wearer.

As an alternative, the monitoring can be done at the optician store, and the optician can propose to the wearer different activities corresponding to the activities of the wearer. For example, the optician can propose to the wearer to read a book, a text on a tablet, to perform different visual tests, for example track or stare at specific visual target, look straight, to test a posture, for example when working on a computer.

The specific activities can be for example driving, sporting, reading, computing. This activity includes indoor and outdoor activities, and near vision intermediate vision and far vision activities.

Before starting the monitoring, a set of tests or calibration can be conducted, preferably at the optician store.

For example, the power and type (single vision, progressive) of the lens necessary to correct the wearer are determined, and the eye tracking device can be equipped with lens having this power and type.

Furthermore, the characteristics of the equipment and/or the wearer may be determined and stored as additional data to improve the optimizing step. For example, it's possible to store the power/type of lens of the equipment, the position of the lens according to the eyes, including the distance between the lens and the eye rotation center, the pantoscopic angle, the pupillary distance, the position of the far vision point according to the frame, the position of the near vision point for a progressive lens, the frame shape of the equipment.

For example, the wearer is equipped with the eye tracking device, and is asked to stare at different visual targets for different known direction. The wearer can for example start at a target at distance, straight away, so as to adopt a primary gaze posture.

During the monitoring step any parameters relating to the eyes of the wearer may be monitored.

For example during the monitoring step one or any combination of the following parameters can be monitored:
 eye gazing direction,
 pupil diameter,
 pupil shape,
 pupil appearance,
 phoria measurements,
 blinking frequency, and
 gazing disparity between both eyes of the wearer
 the convergence distance of the eyes of the wearer,
 the level of illumination of at least one eye of the wearer,
 the intersection of the visual axe of the wearer with at least one surface of the optical lens,
 general eye appearance, such as Iris, cornea, sclera appearance, eye watering, and
 speed of the eye movement.

Such parameter may be used to determine the visual behavior of the wearer, individual parameters, the environment impact of his/her visual activity, a visual strength or fatigue, a ocular disease coming or evolution.

During the monitoring step, additional sensors can be used so as to determine what is the current activity of the wearer or his/her environment. For example, using the accelerometer, it is possible to detect if the wearer is reading or looking straight away. A camera taking pictures of the wearer environment may also be used to determined some kinds of activities, for example is the wearer is driving, or having sport, and if ambient luminance is low or high. For example, an analysis of the motion of the environment is determined from the pictures to detect dynamic activities, such as sport, or to detect moving objects such as cars when driving, or to detect the presence of a video display when using a computer/tablet/smartphone.

The camera can determine the luminance of the environment so as determine if there is a low/high light condition, and determine is any glare sources or fog may be present.

The data collected during the monitoring step can be post treated to determine further information such as the dominant eye of the wearer or identify the area of the optical lens that is the most used by the wearer depending on the type of activity of the wearer.

For example, the eye tracking device may measure the gazing direction for far vision activity, and the position impact on the frame shape of the gazing direction. Similarly, the eye tracking device may measure the gazing direction for near vision activity, and the position impact on the frame shape of the gazing direction.

The vertical distance between the position impacts may be used to define the distance between the fitting cross and the near vision location in a progressive lens.

The far vision activity can be determined when the gaze direction is close to the horizontal and the near vision can be determine when the gaze direction is oriented toward the bottom of the frame shape.

A simple example may be to determine the area of the optical lens the most used by the wearer for gazing at far distant objects and the area of the optical lens the most used by the wearer for gazing at near distant objects.

Advantageously having the wearer used the eye tracking device over a long period of time allows determining for example if along the day the area for gazing at far distances and/or near distances changes.

Although not represented on FIG. 1, the method according to the invention may further comprise a display step during which the information relating to the at least one parameter monitored during the monitoring step is displayed for example to the wearer and/or to an eye care professional.

Furthermore, the method may comprise a sending step during which the information relating to the at least one parameter monitored during the monitoring step is sent to a distant entity for example to a distant server. Advantageously, the lens provider and/or the wearer and/or the eye car professional may access to the information.

During the optimization step the optical lens equipment is optimized based at least partly on the information relating to the wearer eye monitored during the wearer parameter monitoring step.

The optimization may be carried out in different manner depending for example on the type of ophthalmic lens and the type of parameter monitored.

According to an embodiment, the optimization of the optical lens equipment comprises optimizing the optical function of the optical lenses of the optical lens equipment.

In the sense of the invention, the optical function corresponds to a function providing for each gaze direction the effect of the optical lens on the light ray passing through the optical lens.

The optical function may comprise dioptric function, light absorption, polarizing capability, reinforcement of contrast capacity, etc . . . .

The dioptric function corresponds to the optical lens power (mean power, astigmatism etc . . . ) as a function of the gaze direction. The dioptric function may be optimized using the method according to the invention.

Typically, if the ophthalmic lens is a progressive addition lens the method according to the invention may be used to optimize various parameters of the optical lens among which the relative positions of the near and far vision zones and/or the type of design and/or the length of progression and/or the size of the progressive corridor.

In the sense of the invention a progressive addition lens is an ophthalmic lens having a far vision zone, a near vision zone, and a progressive corridor (or channel) there between. The progressive corridor provides a gradual power progression from the far vision zone to the near vision zone without dividing line or prismatic jump.

In the sense of the invention the length of progression of a progressive addition lens corresponds to the distance measured vertically over the lens surface between the fitting cross and a point on the meridian line at which the mean sphere has a difference of 85% relative to the mean sphere at the far vision point.

The wording "optical design" is a widely used wording known from the man skilled in the art in ophthalmic domain to designate the set of parameters allowing defining a dioptric function of an ophthalmic lens; each ophthalmic lens designer has its own designs, particularly for progressive ophthalmic lenses. As for an example, a progressive ophthalmic lens "design" results of an optimization of a progressive surface so as to restore a presbyope's ability to see clearly at all distances but also to optimally respect all physiological visual functions such as foveal vision, extra-foveal vision, binocular vision and to minimize unwanted astigmatisms. For example, a progressive lens design comprises:

a power profile along the main gaze directions (meridian line) used by the lens wearer during day life activities,
distributions of powers (mean power, astigmatism, . . . ) on the sides of the lens, that is to say away from the main gaze direction.

These optical characteristics are part of the "designs" defined and calculated by ophthalmic lens designers and that are provided with the progressive lenses. For example, it is possible to detect if the wearer is in a category of eye mover or a category of head mover, or any intermediate category, by measuring the range of gazing direction of the eyes (horizontal or vertical).

Then, if the wearer is of a category of eye mover, a progressive hard design will be proposed, whereas if the wearer is head mover, a soft design will be proposed, whereas a tradeoff between hard/soft designs will be proposed for intermediate category.

The category can be determined based on the minimum/maximum or the variance of the gaze direction.

The size of the optical lens to be provided to the wearer may also be optimized with the method according to the invention. Indeed, the method according to the invention can provide information on the size of the area of the optical lens used by the wearer. Each wearer may use are of different sizes, therefore the size of the optical lens may be adjusted to correspond to the needs of the wearer.

The optimization of the optical lens may consist in optimizing the position of the optical lens in the spectacle frame. In particular the position of a reference point of the optical lens, such as the prism reference point, relative to the eye of the wearer may be optimized by a method according to the invention.

For example, it is possible to measure over a long period the gaze direction for far vision, take the average gaze direction, determine the impact of this average gaze direction with the frame shape and then position the fitting cross of a progressive lens at this location.

The optimization step according to the invention may consist in selecting a specific optical lens, for example a specific optical lens design, among a list of available optical lens. The selection of the most appropriate optical lens being done based on the monitoring to the eye related parameters.

For example, it is possible to select a progressive lens within a list of progressive lenses proposing different length of progression, different designs (soft design, hard design)

According to an embodiment of the invention the transmission function of the optical lens can be optimized. In the sense of the invention the transmission function corresponds to a function providing for each gaze direction the average transmission over a range of wavelength. The average transmission over a range of wavelength corresponds to the percentage of intensity of the incident light within the corresponding range of wavelength that is transmitted through the optical system.

For example, the luminance measured by camera one the eye may be used to propose different transmission function, for example category between 0-4 (ISO8980-3) adapted to the wearer environment, or to propose specific UV cut-off solution, for example Crizal UV AR coatings, or polarized lenses.

According to an embodiment of the invention, the optimization can take the form of a prescription of specific types of lenses to the wearer. For example, if the wearer monitoring shows frequent watering of the eye to reddish glow revealing visual fatigue, lens reducing visual strength can be proposed to the wearer. An example of lens is Antifatigue™ Lenses from Essilor.

According to an embodiment of the invention, the optimization method according to the invention can be used to optimize classic optical lenses that are manufactured and edged to fit in a spectacle frame, for example the same type of spectacle frame as the one used for the eye tracking device.

The method according to the invention allows improving wearer eye parameter measurement done with the eye tracker device in measuring eye parameter in relationships with the visual environment, for example visual scene and the task or activity performed by the wearer.

The measurement of the eye parameter in relation with the visual environment or activity performed can lead to improved visual equipment for the wearer, since the wearer parameter (for example gaze direction) may depend on the activity. For example, visual strategy may greatly differ for a wearer between a walking activity, or when climbing stairs.

The monitoring step of the eye parameter may include visual scene or activity tracking by mean supplementary devices such as scene camera or inertial sensor or by mean a protocol such as traditionally used in opticians to determine primary gaze direction. For example, the scene camera can be used to have an image of the environment of the wearer, and determine if the wearer if walking on a pavement, doing sport, climbing stairs, driving. etc. using image processing techniques.

It is so possible to define different activities, and store the wearer visual parameters (gaze direction for example) for each of these activities.

Additional parameters, for example the features the wearer is looking during the activity can also be stored (for example, it is possible to store what part of the stairs the wearer if looking when climbing stairs, what are the visual stimuli he will look at when driving . . . ), for example the head rotation if using accelerometer of inertial sensor.

Then, according to the optimization step during which the optical lens equipment is optimized based at least partly on the base of the monitoring of the at least one parameter and at least one parameter of the visual scene and/or the activity of the wearer during the wearer parameter monitoring step.

For example, eye-coordination is measured during natural activity of displacement in a crowd in order to identify the best and natural eye-head coordination used by the wearer in risky collision task. For that, the wearer may be equipped with eye tracking device mounted on a spectacle frame and supplementary devices: a scene camera allows recording the scene. The gyroscope sensor allows recording the head position.

A monitoring phase may be performed to calibrate the head and eye tracking devices in the world reference frame. A synchronized recording of the devices allows linking the appearance of the risk in visual scene and the corresponding eye-head coordination. With this monitoring, it possible to assign to each individual wearer a coefficient that qualifies his propensity to rather move the head or rather move the eyes (head mover/eye mover) in risky collision task. So, it is possible to optimize the optical lens equipment not only according to visual wearer parameter, but also according to parameter related to the activity.

The monitoring phase based on the eye tracking mounted on a spectacle frame device and additional sensor devices improves the head-eye movement ratio measurement obtained with the device developed and commercialized by the applicant under the trademark Varilux Ipseo in order to improve customizing vision correction. This device is used to measure the head-eye movement ratio, which corresponds to a visual imprint of the particular wearer, and personalized progressive lenses are manufactured after processing the data to create a design which matches physiological characteristics of the wearer.

Then, the optimization phase consists of used this behavioral coefficient which presides over calculation of the best suited design. Thus, for example, for a wearer who tends to move the eyes rather than the head, a design having a fairly wide sharp vision field will be chosen, in other words having a high power gradient. Such design is called a hard design. Nevertheless, such design generates more distortions. As against this, for a wearer who rather tends to move more the head than the eyes, soft progression at the periphery will be chosen to avoid an impression of swaying. Such design having a smoother power gradient is called a soft design.

Therefore, the invention also relates to a method of manufacturing an ophthalmic lens for a wearer, the method comprising:
  an optical function optimization step during which the optical function of the ophthalmic lens is optimized using a method according to the invention, and
  a manufacturing step during which the optical lens is manufactured.

Furthermore, the optimization method according to the invention can be used to optimize the optical function of an adjustable lens, for example a programmable lens.

Figure 3:
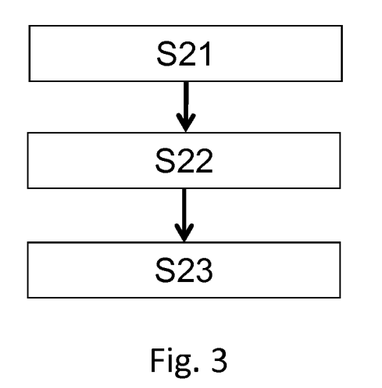
FIG. 3 is a flowchart representing the steps of a method of controlling an adjustable lens device according to the invention.

Therefore as illustrated on FIG. 3, the invention further relates to a method of controlling an adjustable lens device, the method may comprise:
  an adjustable lens device providing step S21,
  an optical function optimization step S22, and
  an optical function adapting step S23.

During the adjustable lens device providing step S21, an adjustable lens device comprising at least an adjustable lens, for example a programmable lens, an optical function controller and an eye tracking device is provided.

The adjustable lens has an optical function and extends between at least one eye of the wearer and the real world scene when the device is used by the wearer.

The optical function controller is arranged to control the optical function of the adjustable lens.

For example, a programmable lens may comprise a set of cells juxtaposed parallel to a surface of the optical lens, forming so called pixelated optical elements.

Such pixelated optical element can also have various optical functions, such as dioptric function, light absorption, polarizing capability, reinforcement of contrast capacity, etc . . . .

The dioptric function of the optical element can be characterized by an optical phase-shift distribution for a given monochromatic light wave which crosses the optical element.

In a general way, the transparent optical element has a surface which extends transversally compared to an optical axis. An average direction of propagation of the light wave can then be selected to be superimposed on this axis, and the optical phase-shift distribution can be given inside the surface element.

In case of pixelated optical elements, optical phase-shift has discrete values which are carried out in point which constitute a sampling of the useable surface of the transparent optical element.

It is well-known that optical phase-shift $\Delta\varphi$ for a monochromatic light wave is equal to the product of the double of number pi by the length of crossing L of each cell, and by the difference between the value n of refraction index of the transparent material which fills the cell and the value of the air refraction index and by the inverse wavelength $\lambda$.

As for the example of FIG. 1, the adjustable lens device is provided with an eye tracking device.

During the optical function optimization step S22, the optical function of the adjustable lens is optimized using an optimization method according to the invention.

During the optical function adapting step S23 the optical function of the adjustable lens is adjusted to correspond to the optimized optical function determined during the optical function optimization step S23.

According to an embodiment of the invention, it is proposed to display information relative to the gaze direction of the wearer. For example, for a progressive lens, it is proposed to display on a computer display a map representing at least one of the right or left lens, for which far vision position, near vision position is represented, and the distribution of the gaze direction within the lens is also represented. This shows to the wearer if his/her gaze direction for near vision/far vision fit the near vision or far vision position on the lens.

It is also possible to represent the width of the field of view for near vision, far vision, or intermediate vision, and then check if the gaze direction distribution falls in the width of the near/far/intermediate field of vision. This will show to the wearer if he/she needs a lens having a larger or reduced width of visual field.

The contour of the width of the visual field can for example be defined as being Iso lines for which unwanted astigmatism has 0.5 D value.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for optimizing optical lens equipment for a wearer, the method comprising:
   an eye tracking device providing step, during which a spectacle frame mounted eye tracking device is provided to the wearer, the eye tracking device including at least one pair of electrodes configured to measure the electrical potential on the skin near the eye of the wearer, and associated processing circuitry configured to detect blinks, saccades and/or eye movements;
   a wearer parameter monitoring step, during which at least one parameter relating to eyes of the wearer is monitored using the eye tracking device, the at least one wearer parameter monitored during the monitoring step being selected from a list consisting of blinking frequency and speed of the eye movement; and
   an optimization step, during which the optical lens equipment is optimized based at least partly on a basis of monitoring of the at least one parameter during the wearer parameter monitoring step, wherein
   when the at least one wearer parameter monitored during the monitoring step comprises speed of the eye movement, then the at least one wearer parameter is used to determine a visual behavior of the wearer and a visual strength or fatigue of the wearer, and wherein during the optimization step, the optical lens equipment is optimized based on the visual behavior of the wearer and the visual strength or fatigue of the wearer, and
   wherein the optical lens equipment is spectacles having prescription ophthalmic lenses.

2. The method according to claim 1, further comprising:
   a visual environment data providing step, during which visual environment data indicative of a visual environment of the wearer is provided; and
   optimizing the optical lens equipment based on at least partly on the visual environment data during the optimization step.

3. The method according to claim 1, comprising a wearer activity data providing step during which wearer activity data indicative of activity of the wearer is provided, and during the optimization step the optical lens equipment is optimized based at least partly on the wearer activity data.

4. The method according to claim 3, further comprising monitoring at least one of the visual environment of the wearer and in a synchronized manner with the wearer parameter so as to link the wearer parameter with at least one of the visual environment of the wearer.

5. The method according to claim 4, further comprising a head movement monitoring step during which head movement of the wearer is monitored in a synchronized manner with the wearer parameter and at least one of the visual environment of the wearer and so as to link eye-head coordination of the wearer with at least one of the visual environment of the wearer.

6. The method according to claim 1, further comprising optimizing an optical function of the optical lens equipment during the optimization step.

7. The method according to claim 1, further comprising selecting, during the optimization step, a specific optical lens from a list of optical lenses on the base of the monitoring of the at least one parameter.

8. The method according to claim 1, further comprising optimizing a position of an optical lens in the optical lens equipment during the optimization step.

9. The method according to claim 1, further comprising adapting the eye tracking device to determine a gazing direction or a viewing distance of the wearer.

10. The method according to claim 1, further comprises further comprising a display step, during which information relating to the at least one parameter monitored during the monitoring step is displayed to the wearer.

11. The method according to claim 1, wherein the eye tracking device further comprises at least one of an accelerometer, and a camera configured to take pictures of at least one of an environment, a light sensor, and a gyroscope sensor.

12. The method according to claim 1, further comprising performing the monitoring step while having the wearer practice specific activities in a natural environment.

13. The method according to claim 1, further comprising monitoring at least one of an amplitude, a variation over time, and a distribution of the at least one parameter during the monitoring step.

14. The method according to claim 1, wherein at least one additional parameter monitored during the monitoring step is selected from the group consisting of:
   eye gazing direction,
   pupil diameter,
   pupil shape,
   pupil appearance,
   phoria measurements,
   blinking frequency,
   gazing disparity between both eyes of the wearer,
   convergence distance of the eyes of the wearer,
   a level of illumination of at least one of the eyes of the wearer,
   an intersection of visual ayes of the wearer with at least one surface of an optical lens,
   general eye appearance, such as an iris, a cornea, a sclera appearance, and eye watering, and
   speed of eye movement.

15. The method according to claim 3, further comprising monitoring the activity of the wearer in a synchronized manner with the wearer parameter so as to link the wearer parameter with the activity of the wearer.

16. The method according to claim 1, Wherein the at least one wearer parameter monitored during the monitoring step is the speed of the eye movement and the at least one wearer parameter is used to determine a visual behavior of the wearer and a visual fatigue of the wearer, and wherein during the optimization step, the optical lens equipment is optimized based on the visual behavior of the wearer and the visual fatigue of the wearer.

17. The method according to claim 16, further comprising instructing manufacture of new ophthalmic lenses for the spectacles based on the visual behavior of the wearer and the visual fatigue of the wearer determined during the optimization.

18. A method of manufacturing an ophthalmic lens for a wearer, the method comprising:
   an optical function optimization step during which an optical function of the ophthalmic lens is optimized by:
   providing a spectacle frame mounted eye tracking device to the wearer, the eye tracking device including at least one pair of electrodes configured to measure the electrical potential on the skin near the eye of the wearer, and associated processing circuitry configured to detect blinks, saccades and/or eye movements;

monitoring at least one parameter relating to eyes of the wearer using the eye tracking device, the at least one wearer parameter monitored being selected from a list consisting of: blinking frequency and speed of the eye movement; and optimizing the ophthalmic lens by optimizing a size of an optical lens based at least partly on a base of the monitoring of the at least one parameter; and a manufacturing step during which the ophthalmic lens is manufactured, wherein when the at least one wearer parameter monitored during the monitoring comprises speed of the eye movement, then the at least one wearer parameter is used to determine a visual behavior of the wearer and a visual strength or fatigue of the wearer, and wherein during the optimizing, the optical lens equipment is optimized based on the visual behavior of the wearer and the visual strength or fatigue of the wearer, and wherein the optical lens equipment is spectacles having prescription ophthalmic lenses.

19. A method of controlling an adjustable lens device comprising an adjustable lens, an optical function controller and an eye tracking device, the adjustable lens comprising an optical function, the adjustable lens extending between at least one eye of a wearer and a real world scene when the device is used by the wearer, the optical function controller being arranged to control the optical function of the adjustable lens, and the eye tracking device including at least one pair of electrodes configured to measure the electrical potential on the skin near the eye of the wearer, and associated processing circuitry configured to detect blinks, saccades and/or eye movements, the method comprising:

an optical function optimization step during which the optical function of the adjustable lens is optimized by:
providing a spectacle frame mounted eye tracking device to the wearer;
monitoring at least one parameter relating to eyes of the wearer using the eye tracking device, the at least one wearer parameter monitored being selected from a list consisting of: blinking frequency and speed of the eye movement; and
optimizing the optical function of the adjustable lens by optimizing a size of an optical lens based at least partly on a base of the monitoring of the at least one parameter; and an optical function adapting step during which the optical function of the adjustable lens is adjusted to correspond to the optimized optical function determined during the optical function optimization step, wherein when the at least one wearer parameter monitored during the monitoring comprises speed of the eye movement, then the at least one wearer parameter is used to determine a visual behavior of the wearer and a visual strength or fatigue of the wearer, and wherein during the optimizing, the optical lens equipment is optimized based on the visual behavior of the wearer and the visual strength or fatigue of the wearer, and wherein the optical lens equipment is spectacles having prescription ophthalmic lenses.

20. A computer program product stored on a non-transitory computer readable medium comprising one or more stored sequences of instructions that are accessible to a processor and which, when executed by the processor, causes the processor to:

monitor at least one parameter relating to eyes of the wearer using an eye tracking device, the eye tracking device including at least one pair of electrodes configured to measure the electrical potential on the skin near the eye of the wearer, and associated processing circuitry configured to detect blinks, saccades and/or eye movements, the at least one wearer parameter monitored being selected from a list consisting of: blinking frequency and speed of the eye movement; and optimize optical lens equipment by optimizing a size of an optical lens based at least partly on a base of monitoring of the at least one parameter monitored by the eye tracking device, wherein when the at least one wearer parameter monitored during the monitoring comprises speed of the eye movement, then the at least one wearer parameter is used to determine a visual behavior of the wearer and a visual strength or fatigue of the wearer, and wherein during the optimizing, the optical lens equipment is optimized based on the visual behavior of the wearer and the visual strength or fatigue of the wearer, and wherein the optical lens equipment is spectacles having prescription ophthalmic lenses.

* * * * *